US008273362B2

(12) United States Patent
Philips et al.

(10) Patent No.: US 8,273,362 B2
(45) Date of Patent: Sep. 25, 2012

(54) OPHTHALMIC EMULSIONS CONTAINING PROSTAGLANDINS

(75) Inventors: Betty Philips, Antony (FR); Séverine Bague, Epinay sur Orge (FR); Laura Rabinovich-Guilatt, Paris (FR); Grégory Lambert, Chatenay Malabry (FR)

(73) Assignee: Novagali Pharma S.A., Evry (FR)

( * ) Notice: Subject to any disclaimer, the term of this patent is extended or adjusted under 35 U.S.C. 154(b) by 109 days.

(21) Appl. No.: 11/667,129

(22) PCT Filed: Oct. 10, 2005

(86) PCT No.: PCT/EP2005/011648
§ 371 (c)(1),
(2), (4) Date: Jun. 4, 2007

(87) PCT Pub. No.: WO2006/050836
PCT Pub. Date: May 18, 2006

(65) Prior Publication Data
US 2008/0107738 A1    May 8, 2008

(30) Foreign Application Priority Data

Nov. 9, 2004  (EP) .................................... 04292645

(51) Int. Cl.
*C07C 405/00* (2006.01)
*A61K 9/107* (2006.01)
*A61P 27/02* (2006.01)
(52) U.S. Cl. .................. 424/400; 424/78.04; 424/489; 514/954; 554/117
(58) Field of Classification Search .................... None
See application file for complete search history.

(56) References Cited

U.S. PATENT DOCUMENTS

| | | | |
|---|---|---|---|
| 4,599,353 A | | 7/1986 | Bito |
| 4,684,633 A | | 8/1987 | Imagawa et al. |
| 5,496,811 A | * | 3/1996 | Aviv et al. ................ 514/78 |
| 5,510,383 A | * | 4/1996 | Bishop et al. .............. 514/530 |
| 5,588,559 A | * | 12/1996 | Vallet Mas et al. ........... 222/92 |
| 5,688,819 A | | 11/1997 | Woodward et al. |
| 5,767,153 A | * | 6/1998 | Bowman et al. ............ 514/530 |
| 5,849,792 A | * | 12/1998 | Schneider .................. 514/530 |
| 6,007,826 A | * | 12/1999 | Benita et al. ................ 424/401 |
| 6,011,062 A | | 1/2000 | Schneider et al. |
| 6,225,348 B1 | * | 5/2001 | Paulsen .................... 514/530 |
| 6,344,477 B1 | * | 2/2002 | Sharif ..................... 514/530 |
| 2002/0136771 A1 | * | 9/2002 | Parr et al. .................. 424/488 |

FOREIGN PATENT DOCUMENTS

| | | |
|---|---|---|
| EP | 0 423 697 | 4/1991 |
| EP | 0 696 452 | 2/1996 |
| EP | 1 532 981 | 5/2005 |
| EP | 1 547 599 | 6/2005 |
| KR | 2003-0046553 | 6/2003 |
| WO | 03/053405 | 7/2003 |

OTHER PUBLICATIONS

RP Bell. "A New Ophthalmic Irrigating Solution: Cetyldimethylbenzylammonium Chloride." Am J Ophthalmol. Sep. 1951;34(9) pp. 1321-1322.*
Woo-Jeong Choi et al., "Low toxicity of cationic lipid-based emulsion for gene transfer", Biomaterials, 2004, pp. 5893-5903, vol. 25, Elsevier Ltd.
Gary Ott et al., "A cationic sub-micron emulsion (MF59/DOTAP) is an effective delivery system for DNA vaccines", Journal of Controlled Release, 2002, pp. 1-5, vol. 79, Elsevier Science B.V.
Satoshi Ogawa et al., "Production and Characterization of O/W Emulsions Containing Cationic Droplets Stabilized by Lecithin-Chitosan Membranes", Journal of Agricultural and Food Chemistry, 2003, pp. 2806-2812, vol. 51, American Chemical Society.
Shunmugaperumal Tamilvanan et al., "The potential of lipid emulsion for ocular delivery of lipophilic drugs", European Journal of Pharmaceuticals and Biopharmaceuticals, 2004, pp. 357-368, vol. 58, Elsevier B.V.
Caroline Debbasch et al., "Quarternary Ammoniums and Other Preservatives' Contribution in Oxidative Stress and Apoptosis on Chang Conjunctival Cells", Investigative Ophthalmology & Visual Science, Mar. 2001, pp. 642-652, vol. 42, No. 3, Association for Research in Vision and Ophthalmology.
Abstract of S. Klang et al., "Influence of emulsion droplet surface charge on indomethacin ocular tissue distribution", Pharm. Dev. Technol., 2000, pp. 521-532, vol. 5.
C. Washington, "Stability of lipid emulsions for drug delivery", Advanced Drug Delivery Reviews, 1996, pp. 131-145, vol. 20, Elsevier Science B.V.
Laura Rabinovich-Guilatt et al., "Extensive surface studies help to analyse zeta potential data: the case of cationic emulsions", Chemistry and Physics of Lipids, 2004, pp. 1-13, vol. 131, Elsevier Ireland Ltd.
Abstract of F. Liu et al., "New cationic lipid formulations for gene transfer", Pharm Res., 1996, pp. 1856-1860.
Shmuel H. Klang et al., "The stability of piroxicam incorporated in a positively-charged submicron emulsion for ocular administration", International Journal of Pharmaceutics, 1996, pp. 33-44, vol. 132, Elsevier Science B.V.
Abstract of N.J. Zuidam et al., "Chemical hydrolysis of phospholipids", J Pharm Sci, Sep. 1995, pp. 1113-1119, vol. 84.
F.S. Varveri et al., "Chemiluminescence monitoring of hemolysis by lysophospholipids", Journal of Photochemistry and Photobiology A, 1995, pp. 121-124, vol. 31, Elsevier Science S.A.

(Continued)

*Primary Examiner* — Frederick Krass
*Assistant Examiner* — Isaac Shomer
(74) *Attorney, Agent, or Firm* — Young & Thompson

(57) ABSTRACT

Cationic ophthalmic oil-in-water type emulsions, include colloid particles having an oily core surrounded by an interfacial film, the emulsion including at least one cationic agent and at least one non ionic surfactant, the oily core including a prostaglandin selected from the group comprising in particular latanoprost, unoprostone isopropyl, travoprost, bimatoprost, tafluprost, 8-isoprostaglandin$E_2$, or a mixture thereof, for treating ocular hypertension and/or glaucoma. These emulsions have the property to increase the chemical stability of prostaglandins.

19 Claims, 1 Drawing Sheet

OTHER PUBLICATIONS

S. Tamilvanan et al., "Ocular delivery of cyclosporin A—I. Design and characterization of cyclosporin A-loaded positively-charged submicron emulsion", S.T.P. Pharma Sciences, 2001, pp. 421-426, vol. 6.

Muhannad Jumaa et al., "Physicochemical properties of chitosan-lipid emulsions and their stability during the autoclaving process", International Journal of Pharmaceutics, 1999 pp. 175-184, vol. 183, Elsevier Science B.V.

Muhannad Jumaa et al., "A new lipid emulsion formulation with high antimicrobial efficacy using chitosan", European Journal of Pharmaceuticals and Biopharmaceuticals 2002, pp. 115-123, vol. 53, Elsevier Science B.V.

Abstract of S.H. Klang, et al., "Physicochemical characterization and acute toxicity evaluation of a positively-charged submicron emulsion vehicle", Pharm. Pharmacol., Dec. 1994, pp. 986-993, vol. 46.

Abstract of P. Furrer et al., "Ocular tolerance of preservatives and alternatives", Eur. J. Pharm. Biopharm., May 2002, pp. 263-280, vol. 53.

Abstract of J. Han et al., "Partition of antimicrobial additives in an intravenous emulsion and their effect on emulsion physical stability", Int. J. Pharm., Jan. 20, 2005, pp. 263-271, vol. 288.

Abstract of M. Sznitowska et al., "Physicochemical screening of antimicrobial agents as potential preservatives for submicron emulsions", Eur. J. Pharm. Sci., Jun. 2002, pp. 489-495, vol. 15.

* cited by examiner

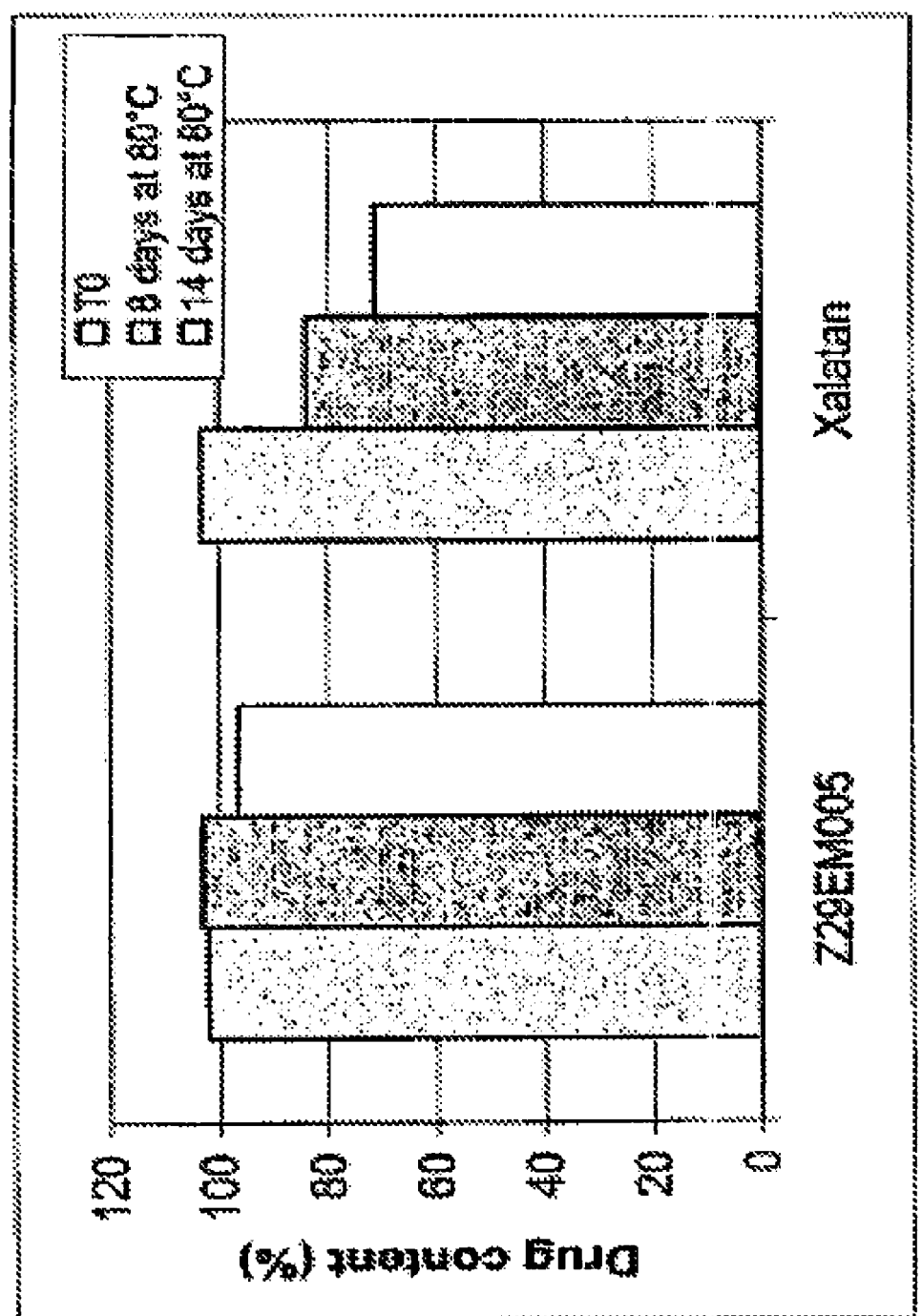

OPHTHALMIC EMULSIONS CONTAINING PROSTAGLANDINS

FIELD OF THE INVENTION

The present invention concerns ophthalmic cationic oil-in-water type emulsions containing prostaglandins.

In the present invention, the term <<prostaglandin >> is indifferently used for prostaglandin, its precursors or analogs.

The present invention is of particular interest for prostaglandin $F_{2\alpha}$ analogs such as in particular latanoprost, unoprostone isopropyl, travoprost, bimatoprost, tafluprost, 8-isoprostaglandin $E_2$.

By <<ophthalmic >> it is meant an emulsion intended to be applied to the eye and which presents a pharmaceutical effect, preferably, it is topically applied.

BACKGROUND OF THE INVENTION

It is known to use prostaglandins in ophthalmic preparations in order to treat glaucoma.

The problem encountered with prostaglandins, in particular with latanoprost, is that they are particularly chemically unstable.

U.S. Pat. No. 6,011,062, U.S. Pat. No. 5,688,819, U.S. Pat. No. 5,849,792, U.S. Pat. No. 4,599,353 describe the use of several prostaglandin analogs for treating glaucoma and ocular hypertension. EP 1 532 981 and EP 1 547 599 describe eye-drops containing latanoprost. Said patent applications describe aqueous and transparent solutions of latanoprost in which benzalkonium chloride (BAK) is used as a solubilising agent. Most of the ophthalmic solutions described the use of BAK as a solubilising agent for the prostaglandin. The prostaglandins, in particular latanoprost, are thus present in a micellar systems. U.S. Pat. No. 5,849,792 discloses the use of a non ionic surfactant (polyethoxylated castor oil) to enhance the prostaglandin's chemical stability.

However, the proposed solutions to enhance the stability of prostaglandins are not completely satisfactory. Furthermore, use of BAK or other quaternary ammonium as preservative or solubilising agent for prostaglandins in ophthalmic preparations has been challenged, since C, Debbasch et al. in Investigative Ophthalmology & Visual Science, March 2001, Vol 42 n° 3, demonstrated important toxicity of long term use of BAK and/or other quaternary ammoniums.

Latanoprost, Travoprost, Bimatoprost, unoprostone isopropyl, tafluprost, 8-isoprostaglandin$E_2$, like most of the prostaglandin analogs, are almost insoluble in water. So, it is interesting to provide ophthalmic vehicles suitable for delivering hydrophobic drugs. In recent years, oil-in-water type emulsions, in particular emulsions having droplets of a submicron size (hereinafter "submicron emulsions") gained increasing importance.

However, stabilizing emulsions, including submicron emulsions, may be a concern for one skilled in the art. One known approach to stabilize an emulsion is to confer an electrostatic charge to the droplets surface which will result in droplet repulsion and less droplet coalescence. Colloidal particles dispersed in a solution are electrically charged due to their ionic characteristics and dipole attributes. This charge, which can be negative resulting in anionic emulsions or positive producing cationic emulsions (Klang et al., Pharm. Dev. Technology 2000, 5, 521-532) is known in the art as the "zeta potential". The zeta potential is a measure of the magnitude of the repulsion or attraction between particles (Washington, Adv. Drug Deliv. Reviews 1996, 20:131-145).

Formulations of submicron emulsions reported in the literature are usually based on a combination of lecithins which are mixtures of phospholipids of various compositions obtained from natural sources, non-ionic or ionic surfactants and of oil such as vegetable oil. Lecithins generally comprise as major components phosphatidylcholine, which is neutral over a wide pH range, negatively charged phospholipids such as phosphatidylserine and phosphatidic acid and positively charged phospholipids such as phosphatidylethanolamine. As a consequence of their composition, the colloid particles in most available phospholipid-based emulsions are negatively charged. Addition of sufficient amounts of cationic agents such as stearylamine, oleylamine, chitosan, {N-[i-(2, 3-dioleoyloxy)propyl]-N,N,N-trimethyiammonium (DOTAP) or others can reverse this surface charge and produce a positively-charged colloid, as reflected by their zeta potential (Rabinovich-Guilatt et al., Chem Phys Lipids 2004, 131:1-13; Liu et al., Pharm. Res. 1996, 13:1856-1860, Klang et al., Int. J. Pharm. 1996, 132:33-44).

In all phospholipid-containing colloids (e.g. liposomes or emulsions), a significant decrease in zeta potential is observed overtime, due to the hydrolysis of phospholipids into free fatty acids (Zuidam and Crommelin, J Pharm Sci 1995, 84:1113-1119) which can be a source of toxic side effects following administration (Varveri et al., J. Photochem. Photobiol. A 1995, 91:121-124). In cationic phospholipids colloids, the decrease in zeta potential evidences that the system is not completely chemically stable (Tamilvanan et al., STP Pharma Sciences 2001, 11:421-426) and in some cases could result in the physical destabilization of the formulation as reflected by the droplet size.

For example, in chitosan cationic formulations containing 0.25-1.5% chitosan, 0-1.5% phospholipids, 0-2.5% poloxamer in a castor:soybean oil phase, only the formulation containing poloxamer with chitosan displayed good stability during autoclaving, while the coexistence of chitosan and phospholipids resulted in a destabilization of the emulsion during sterilization. According to the authors, the interaction between the positively charged chitosan with negatively-charged phospholipids which resulted in a damaged emulsifier film around the oil droplets provoked the coalescence of the droplets (Int. J Pharm. 1999, 183:175-84). These emulsions were evaluated further for their antimicrobial activity for mucosal or parenteral administration (Eur. J. Pharm. Biopharm. 2002, 53:115-23).

Of particular interest are the following patents dealing with cationic emulsions for topical ocular administration:

U.S. Pat. No. 6,007,826 discloses a cationic oil-in-water emulsion which comprises colloid particles with a positively charged interfacial film. The interfacial film is formed by cationic lipids (0.05-3% by weight) such as $C_{10}$-$C_{14}$ primary alkylamines (disclosed are stearylamine or oleylamine), $C_{10}$-$C_{24}$ primary alkanolamine or a cholesterol betainate; phospholipids (0.5-3%) and non-ionic surfactants from the group consisting of poloxamers, tyloxapol, polysorbate, and polyoxyethylene fatty acid esters (0.05-3%). The concentration of the oily core is maintained within the 3-20% range.

U.S. Pat. No. 6,007,826 emulsions zeta potential are not stable to thermal stress (see Tamilvanan et al., STP Pharma Sciences 2001, 11:421-426 and Example 12).

SUMMARY OF THE INVENTION

Thus, there is still a need in ophthalmic prostaglandin products which are at least as efficient as the commercial products, which present an enhanced chemical stability of the prostaglandin, which are less toxic, which are more physically stable than conventional products, i.e. which are stable overtime and which present a good tolerability for the patient.

BRIEF DESCRIPTION OF THE DRAWINGS

The sole FIGURE depicts a graphical representation of Latanoprost stability improvement in emulsion compared to commercial product (Xalatan®).

DETAILED DESCRIPTION OF THE INVENTION

By overtime in the meaning of this invention, it is meant a duration exceeding 1 year, preferably exceeding 2 years, more preferably exceeding 3 years.

By "good tolerability" in the present the invention, it is understood that the ratio therapeutic benefit to ocular discomfort is acceptable by the patient, and preferably similar to a placebo or NaCl 0.9% solution.

It is generally accepted that in order to show good ocular tolerability the cation content within the formulation should not exceed 0.1%, preferably not exceed 0.05% and even more preferably should not exceed 0.03%. Primary amines such as stearylamine or oleylamine were shown to be safe for ocular administration at 0.3% w/v (Klang et al., J. Pharm. Pharmacol. 1994, 46:986-993). Quaternary amines such as benzalkonium chloride, benzododecinium bromide and benzethonium chloride are allowed by health authorities for ophthalmic administration up to concentration of approximately 0.03% (Furrer et al., Eur. J. Pharm. Biopharm. 2002, 53:263-280).

Said emulsions are cationic ophthalmic oil-in-water type emulsions, which comprise colloid particles having an oily core surrounded by an interfacial film, said emulsion comprising at least one cationic agent and at least one non ionic surfactant said oily core comprising a prostaglandin or prostaglandin analogue.

In said emulsions, the chemical stability of prostaglandins is enhanced. Without being linked by any theory, it is believed that since the prostaglandin is solubilized in the oily core of the emulsion, it is less available to contact with agents enhancing its degradation. Said stability is defined as the extent to which a product retains, within specified limits and throughout its period of storage and use (i.e., its shelf life), the same properties and characteristics that it possessed at the time of manufacture. The purpose of stability testing is to provide evidence on how the quality of a drug substance or drug product varies overtime under the influence of a variety of environmental factors such as temperature, humidity and light, and enables recommended storage conditions, re-test periods and shelf lives to be established.

Although real-time stability studies include an evaluation of those factors that ultimately affect the expiration date of the drugs, they are time and cost-consuming. Conventionally, accelerated stability studies are used for predicting the shelf life of pharmaceutical products. Such accelerated studies subject the systems to a temperature of 40° C. during 6 months.

In order to understand the intrinsic stability mechanism of the molecule by establishing degradation pathways and identifying the likely degradation products, and thus to adjust the analytical procedures to be used, the Applicant has developed stress stability testing during which the emulsions are subjected to extreme conditions that is a temperature of 80° C. during specified period of time.

Examples of prostaglandins which may be used in the emulsions according to the invention are latanoprost, unoprostone isopropyl, travoprost, bimatoprost, tafluprost, 8-iso-prostaglandinE$_2$ or a mixture of two or more thereof, preferably latanoprost.

The amount of prostaglandins present in the oily core of the emulsion according to the invention depends on the nature of the prostaglandins and to the intended use. And in general, it is 0.001 to 1% w/w, preferably 0.002 to 0.3% w/w and even more preferably 0.004 to 0.15% w/w.

In the present application, percentages are expressed as % w/w with respect to the total weight of the emulsion.

The concentration of the cationic agent is comprised between 0.001 to 0.1% w/w, preferably between 0.002 to 0.05% w/w and even more preferably between 0.003 to 0.03% w/w.

The concentration of the oily core is not higher than 7% w/w, preferably between 0.5 to 5% w/w and even more preferably between 1 to 3% w/w.

The concentration of the non-ionic agent is less than 1% w/w, comprised preferably between 0.01 to 0.6% w/w.

The cationic agent is selected in the group consisting of C10-C24 primary alkylamines, tertiary aliphatic amines, quaternary ammonium compounds selected from the group comprising benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristalkonium halide, stearalkonium halide or a mixture of two or more thereof, halide being preferably chloride or bromide, cationic lipids, amino alcohols, biguanide salts selected from the group comprising chlorhexidine and salts thereof, polyaminopropyl biguanide, phenformin, alkylbiguanide or a mixture of two or more thereof, cationic polymers selected from chitosan, 1,2-dioleyl-3-trimethylammonium-propane,1,2-dioleoyl-sn-glycero-phosphatidylethanolamine, cationic glycosphingo-lipids or cationic cholesterol derivatives, or mixtures of two or more thereof.

According to a preferred embodiment, the cationic agent is selected from the group comprising benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof.

The oily phase of the emulsion may comprise one or more components selected from the group consisting of vegetable oils (i.e. soybean oil, olive oil, sesame oil, cotton seed oil, castor oil, sweet almond oil), mineral oil (i.e. petrolatum and liquid paraffin), medium chain triglycerides (MCT) (i.e. a triglyceride oil in which the carbohydrate chain has about 8-12 carbon atoms), oily fatty acid, isopropyl myristate, oily fatty alcohols, esters of sorbitol and fatty acids, oily sucrose esters, and in general any oily substance which is physiologically tolerated.

The major component of the oily phase will preferably be either vegetable oil and/or MCT. Fatty acids or fatty alcohols may be included in cases where the hydrophobic substance to be carried by the emulsion is not sufficiently soluble in the oily phase.

Examples of MCT oil which may be used in emulsions of the present invention are TCM™ (Société des Oléagineux, France), Miglyol 812™ (Dynamit Novel, Sweden).

The non-ionic surfactant is selected from the group consisting of poloxamers, tyloxapol, polysorbates, polyoxyethylene castor oil derivatives, sorbitan esters, polyoxyl stearates and a mixture of two or more thereof.

According to another preferred embodiment of the invention, the cationic ophthalmic emulsion comprises benzalkonium chloride as cationic agent and tyloxapol as non-ionic surfactant.

According to still another preferred embodiment, the emulsion contains benzalkonium chloride as cationic agent and a combination of tyloxapol and poloxamer as non-ionic surfactants.

Even though benzalkonium chloride (BAK) is classified as a cationic agent, it also presents a preservative function. However, thanks to the specific structure of the emulsions according to the invention, the toxicity due to BAK is reduced as compared to other ophthalmic preparations containing BAK (Han J, Washington C 2005. Partition of antimicrobial additives in an intravenous emulsion and their effect on emulsion physical stability. Int J Pharm 288(2):263-271 and Sznitowska M, Janicki S, Dabrowska E A, Gajewska M 2002. Physicochemical screening of antimicrobial agents as potential preservatives for submicron emulsions. Eur J Pharm Sci 15(5):489-495).

The emulsion may also contain antioxidant such as Vitamin E, isotonic agent, buffering agent, preservative, etc.

The cationic ophthalmic emulsion according to the invention is not transparent since the colloidal particles have an average particle size of equal or less than 1 µm, advantageously equal or less than 300 nm, more advantageously in the range of 100 to 250 nm.

According to another embodiment of the invention, the cationic ophthalmic emulsion may comprise a further pharmaceutically active substance, either in the oily core or in the aqueous part of the emulsion.

Said further antiglaucomateous active substance may be selected from the group comprising beta-blockers such as levobunolol, befundol, metipranolol, cartrolol, timolol; inhibitors of carbonic anhydrase such as brinzolamide, dorzolamide, acetazolamide, methazolamide, dichlorophenamide; sympathomimetics such as brimonidine, apraclonidine, dipivefrine, epinephrine; parasympathomimetics such as pilocarpine; cholinesterase inhibitors such as physostigmine, echothiophate and/or their derivatives; and/or optically acceptable salts thereof.

The emulsions according to the invention are physically stable overtime as defined hereabove and keep a positive zeta potential in the specific measurement conditions as described in Tests A, B, C and/or D.

According to the invention, the emulsions do not contain a sufficient amount of any substances susceptible of affecting the zeta potential overtime. Advantageously, the emulsions of the invention do not contain phospholipids.

Substances susceptible of affecting the zeta potential may be phospholipids, and any substances which become negatively charged upon storage.

The amount of substances affecting the zeta potential overtime must be such that at any time, the amount of positive charge is above the amount of negative charges.

Zeta Potential

Zeta potential measures a physical property which is exhibited by any particle in suspension. Zeta potential can be used to predict behaviour of the suspension in different environments, to optimize the formulations of suspensions and emulsions as well as to predict overtime stability.

In order to avoid the emulsion droplets to adhere to one another and form aggregates of successively increasing size, it is necessary to confer repulsive forces to the particles. One of the means to confer repulsive forces to a colloidal system is by electrostatic or charge stabilization. Electrostatic or charge stabilization has the benefits of stabilizing a system by simply altering the concentration of ions in the system. This is a reversible and inexpensive process.

There might by many origins of this surface charge depending upon the nature of the particle and its surrounding medium but the most important mechanisms are the ionisation of surface groups or the adsorption of charged ions.

The interaction of particles in polar liquids is not governed by the electrical potential at the surface of the particle, but by the effective potential of the particle and its associated ions. To utilize electrostatic control of dispersions, it is the zeta potential of the particle that must be measured rather than its surface charge. Charged particles will attract ions of opposite charge in the dispersant. Ions close to the surface are strongly bound; those further away form a more diffuse region. Within this region is a notional boundary, known as the slipping plane, within which the particle and ions act as a single entity. The potential at the slipping plane is known as the zeta potential. It has long been recognised that the zeta potential is a very good index of the magnitude of the interaction between colloidal particles and measurements of zeta potential are commonly used to assess the stability of colloidal systems. The zeta potential measured in a particular system is dependent on the chemistry of the surface, and also of the way it interacts with its surrounding environment. Therefore zeta potential must always be studied in a well defined environment (specifically pH and ionic strength).

Electrophoretic Mobility

An important consequence of the existence of electrical charges on the surface of particles is that they interact with an applied electric field. These effects are collectively defined as electrokinetic effects. If the motion is induced in a particle suspended in a liquid under the influence of an applied electric field, it is more specifically named electrophoresis. When an electric field is applied across an electrolyte, charged particles suspended in the electrolyte are attracted towards the electrode of opposite charge. Viscous forces acting on the particles tend to oppose this movement. When equilibrium is reached between these two opposing forces, the particles move with constant velocity. The velocity is dependent on the strength of electric field or voltage gradient, the dielectric constant of the medium, the viscosity of the medium and the zeta potential. The velocity of a particle in a unit electric field is referred to as its electrophoretic mobility. Zeta potential is related to the electrophoretic mobility by the Henry equation:

$$U_E = \frac{2\epsilon z f(\kappa a)}{3\eta}$$

where $U_E$=electrophoretic mobility, $z$=zeta potential, $\epsilon$=dielectric constant, $\eta$=viscosity and $f(\kappa a)$=Henry's function.

Electrophoretic determinations of zeta potential are most commonly made in aqueous media and moderate electrolyte concentration. $f(\kappa a)$ in this case is 1.5, and this is referred to as the Smoluchowski approximation. Therefore calculation of zeta potential from the mobility is straightforward for systems that fit the Smoluchowski model, i.e. particles larger than about 0.2 microns dispersed in electrolytes containing more that $10^{-3}$ molar salt. For small particles in low dielectric constant media (eg non-aqueous media), $f(\kappa a)$ becomes 1.0 and allows an equally simple calculation. This is referred to as the Huckel approximation.

Tests A, B, C and D

Test A consists in measuring the stability of the emulsion zeta potential under thermal stress conditions.

Zeta potential of the emulsion is measured at T=0, i.e. as soon as the emulsion has been prepared, the obtained value being named $Z_0$. Glass vials (Type I) of 10 ml effective capacity containing between 5-10 ml of emulsion and sealed under nitrogen atmosphere (without bubbling) are stored at 80° C.

Then at T=15 hours the zeta potential $Z_{15h}$ is measured.

The value $\delta A = Z_{15h} - Z_0$ is then calculated.

For each measurement of the zeta potential, it is operated as follows:

The zeta potential of the emulsion droplet surface is determined by electrophoretic mobility in an apparatus such as a Malvern Zetasizer 2000 (Malvern Instruments, UK) equipped with suitable software and calibrated with the supplied standard.

The emulsion is diluted in double distilled water if needed in order to obtain the scattering intensity allowing optimal particle detection. The sample count rate should be between 100 to 1000 KCps, in homodyne detection (if heterodyne detection is used, the contribution of the reference beam should be deduced). Three consecutive measurements are performed at 25° C. using a constant cell drive of 150 mV. The electrophoretic mobility is converted into zeta potential values through the Smoluchowsky equation, using the dielectric constants and viscosity of water. The measured value corresponds to the average of the 3 obtained values.

It is considered that the emulsion meets zeta potential stability Test A if $\delta A$ is less than the standard error of measurements, preferably less than 10 mV, and even more preferably less than 5 mV.

According to an advantageous embodiment, the ophthalmic emulsion according to the invention meets zeta potential stability Test B.

Test B is similar to Test A except that the emulsion is stored during 48 hours at 80° C., the zeta potential $Z_2$ is measured on day 2 and $\delta B = Z_2 - Z_0$ is calculated. The emulsion is considered as meeting the requirements of zeta potential stability test B if $\delta B$ is less than the standard error of measurements, preferably less than 10 mV, and even more preferably less than 5 mV.

According to a more advantageous embodiment of the invention, the ophthalmic emulsion according to the invention meets zeta potential stability Test C.

Test C is similar to Test A except that the emulsion is stored during 7 days at 80° C., the zeta potential $Z_7$ is measured on day 7 and $\delta C = Z_7 - Z_0$ is calculated. The emulsion is considered as meeting the requirements of zeta potential stability test C if $\delta C$ is less than the standard error of measurements, preferably less than 10 mV, and even more preferably less than 5 mV.

According to a still more advantageous embodiment of the invention, the ophthalmic emulsion according to the invention meets zeta potential stability Test D.

Test D is similar to Test A except that the emulsion is stored during 14 days at 80° C., the zeta potential $Z_{14}$ is measured on day 14 and $\delta D = Z_{14} - Z_0$ is calculated. The emulsion is considered as meeting the requirements of zeta potential stability test D if $\delta D$ is less than the standard error of measurements, preferably less than 10 mV, and even more preferably less than 5 mV.

According to another aspect, the invention relates to a process for manufacturing the emulsions here-above described.

The emulsions are prepared as follows:

the prostaglandin is dissolved into the oily phase, which is optionally added with another hydrophobic ophthalmologically active ingredient, the aqueous phase, optionally added with another hydrophilic ophthalmologically active ingredient, is rapidly added to the oily phase, the coarse emulsion obtained is rapidly heated, preferably at 75° C., the emulsion droplet size is then decreased by any suitable means known by one skilled in the art, for example by shear mixing, the emulsion temperature is cooled down to 20° C. using an ice bath and then homogenized pH is adjusted to 7-8, the emulsion is sterilized.

The inventions also relates to the use of a cationic ophthalmic oil-in-water emulsion as hereabove described for the preparation of an ophthalmic composition for treating ocular hypertension and/or for treating glaucoma.

According to another aspect, the invention relates to ophthalmic formulation comprising an emulsion as previously described, optionally in combination with an ophthalmologically acceptable carrier, in the form of eye drops, eye ointment, ophthalmic gel. In said ophthalmic formulation there may be a pharmaceutically effective amount of an active ingredient in or within the ophthalmologically acceptable carrier.

The invention is also directed to a delivery device selected from the group comprising lenses, ocular patch, implant, insert, said device containing an emulsion as previously described.

The invention is further illustrated by the examples below.

EXAMPLES

In the following examples, the following abbreviations are used:

Medium Chain Triglycerides MCT: TCM™ (Société des Oléagineux)

BAK: benzalkonium chloride (FeF Chemicals, Denmark)

Lutrol: Lutrol F68™ (BASF)

Tyloxapol: Triton WR1339 (Ruger Chemicals, USA)

Z29: latanoprost

Example 1

| Emulsion | Z29EM002 | Z29EM003 | Z29EM005 | Z29EM007 |
|---|---|---|---|---|
| Composition | 1% MCT | 1% MCT | 0.02% BAK | 0.02% BAK |
| | 0.1% Lipoid | 0.1% Tyloxapol | 1% MCT | 1% MCT |
| | 0.05% OA | 0.05% OA | 0.16% Tyloxapol | 0.3% Tyloxapol |
| | 0.005% vit E | 0.005% vit E | 0.01% vit E | 0.01% vit E |
| | 0.25% Lutrol | 0.25% Lutrol | 0.25% Lutrol | 0.1% Lutrol |
| | 2.25% Glycerin | 2.25% Glycerin | 2.25% Glycerin | 2.25% Glycerin |
| | Water to 100% | Water to 100% | Water to 100% | Water to 100% |
| | Z29 0.005% | Z29 0.005% | Z29 0.005% | Z29 0.005% |

| | -continued | |
|---|---|---|
| Zeta potential stress test | T0: 22.4<br>T7: 24.1<br>T15: 19.8 | T0: 21.8<br>T7: 18.8<br>T15: 18.9 |
| Droplet size (nm) stress test | T0: 160<br>T7: 173<br>T15: 185 | T0: 212<br>T7: 225<br>T15: 236 |

| Emulsion | | Z29EM008 | Z29EM011 |
|---|---|---|---|
| Composition | | 0.02% BAK<br>1% MCT<br>0.3% Tyloxapol<br>0.1% Lutrol<br>2.25% Glycerin<br>Water to 100%<br>Z29 0.005% | 0.01% BAK<br>1% MCT<br>0.3% Tyloxapol<br>0.1% Lutrol<br>2.25% Glycerin<br>Water to 100%<br>Z29 0.005% |
| Zeta potential stress test | | T0: 20.6<br>T7: 18.5<br>T15: 16.2 | |
| Droplet size stress test | | T0: 201<br>T7: 212<br>T15: 216 | |

The oily phase components including 0.005% latanoprost (named Z29 in the Tables) were successively weighed in the same beaker and then magnetically stirred under a slight heating (40° C.) until a slightly viscous phase is obtained. Aqueous phase components were successively weighed in the same beaker and then magnetically stirred under a slight heating (40° C.) until a transparent, limpid and fluid phase is obtained. Both phases were heated to 65° C. The coarse emulsion was formed by rapid addition of the aqueous phase in the oily phase and was then rapidly heated to 75° C. The aqueous phase and coarse emulsion beakers were protected by a film to avoid any water evaporation. The emulsion was white and slightly transparent. The emulsion droplet size was then decreased by a 5 minutes high shear mixing with a POLYTRON PT 6100. The emulsion became milky. The emulsion temperature was cooled down to 20° C. using an ice bath.

The final emulsion was obtained by homogenization in a microfluidizer (C5, Avestin) using continuous cycles for 5 min at a pressure of 10,000 psi. The emulsion was milky, very fluid and did not adhere on the glass. The emulsion temperature was decreased to 25° C. Its pH was measured and then adjusted to 7.0 using a 0.1 M HCl or 0.1 M NaOH solution. Emulsion was conditioned in glass vials with nitrogen bubbling and then sterilized in an autoclave 20 minutes at 121° C.

The mean particle size of the emulsions droplets was determined by quasi-elastic light scattering after dilution in water using a High Performance Particle Sizer (Malvern Instruments, UK).

The electrophoretic mobility was measured at 25° C. in a Malvern Zetasizer 2000 (Malvern Instruments, UK) following a 1:200 dilution in double distilled water as detailed above and converted into zeta potential through the Smoluchowski equation.

Example 2

Latanoprost Stability Improvement in Emulsion Compared to Commercial Product (Xalatan®)

The chemical stability of latanoprost within the emulsion was compared to the commercial product Xalatan® at 80° C. for 14 days.

Prostaglandin contents were analysed by an HPLC-UV method.

In emulsions according to the invention, latanoprost is chemically stabilized.

Example 3

In Vivo Studies Demonstrating That Latanoprost emulsion is as Efficient as the Commercial Product (Xalatan®) in Reducing IOP (Intraocular Pressure)

Methods:

Eight adult female cynomolgus monkeys, each weighing 3-6 kg, in which glaucoma had been induced by diode laser photocoagulation of the mid-trabecular meshwork, were used in this study. Intraocular pressure (IOP) was measured at 0 hr (before drug administration) and then hourly until 6 hrs after drug administration for one baseline day, one vehicle-treated day, and treatment days 1,3, and 5 with 30 µl of Z29EM007 (similar to the emulsion described in Example 1) or 0.005% Latanoprost (Xalatan; Pharmarcia & Upjohn, Kalamazoo, Mich.).

The products were topically applied to the glaucomatous eye once daily for 5 consecutive days in a crossover design with a washout period at least 2 weeks between the two drugs.

Results:

Once daily administration of both Z29EM007 and Xalatan for 5 days significantly ($p<0.005$) reduced IOP from 1 hr to 5 hrs after the first dose compared to the vehicle treatment day.

The ocular hypotensive effect was enhanced by repeated dosing for both Z29EM007 and Xalatan. No statistical difference of IOP reduction ($p>0.80$) was observed during the 5 days treatment when comparing Z29EM007 and Xalatan. IOP on the baseline day and vehicle-treated day was not statistically different between the two drugs ($p>0.90$).

Latanoprost in the emulsions according to the invention is as efficient as commercially available Xalatan™.

The invention claimed is:

1. A cationic ophthalmic oil-in-water emulsion, comprising:
    a cationic agent;
    at least one non ionic surfactant;
    colloid particles having an oily core surrounded by an interfacial film;
    said oily core comprising a prostaglandin, wherein,
    the prostaglandin is latanoprost,
    the cationic agent is cetalkonium chloride, and the at least one non ionic surfactant is not a polyoxyethylene castor oil derivative;

wherein the emulsion does not contain phospholipids;

wherein the emulsion contains no substance susceptible of affecting the zeta potential overtime; and wherein the emulsion has a positive zeta potential and meets the zeta potential stability Test A requirements, wherein the requirements comprise:

the difference between the zeta potential measured when the emulsion is prepared and the zeta potential measured after 15 hours of storage is less than the standard of error of measurement, wherein, the storage for 15 hours is in glass vials (Type I) of 10 mL effective capacity containing between 5-10 mL of the emulsion sealed under nitrogen atmosphere (without bubbling) at 80° C., and, the zeta potential is measured by electrophoretic mobility in an apparatus equipped with suitable software and calibrated with the supplied standard, where, the emulsion is diluted in double distilled water to obtain scattering intensity allowing optimal particle detection, a sample count rate between 100 to 1000 KPcs is used in homodyne detection, three consecutive measurements are performed at 25° C. using a constant cell drive of 150 mV, the measurements are averaged, the measurements are converted into zeta potential values through the Smoluchowsky equation, using the dielectric constants and viscosity of water.

2. The cationic ophthalmic oil-in-water emulsion according to claim 1, wherein the amount of said latanoprost in the oily core is 0.001 to 1% w/w.

3. The cationic ophthalmic oil-in-water emulsion according to claim 1, wherein the concentration of the cetalkonium chloride is comprised between 0.001 to 0.1% w/w.

4. The cationic ophthalmic oil-in-water emulsion according to claim 1, wherein the concentration of the oily core is not higher than 7% w/w.

5. The cationic ophthalmic emulsion according to claim 1, wherein the concentration of the non-ionic surfactant is less than 1% w/w.

6. The cationic ophthalmic emulsion according to claim 1, wherein the oil phase comprises one or more components selected from the group consisting of vegetable oils, mineral oil, medium chain triglycerides, oily fatty acid, isopropyl myristate, oily fatty alcohols, esters of sorbitol and fatty acids, and oily sucrose esters.

7. The cationic ophthalmic emulsion according to claim 6, wherein the oil is medium chain triglycerides.

8. The cationic ophthalmic emulsion according to claim 1, wherein the non-ionic surfactant is selected from the group consisting of poloxamers, tyloxapol, polysorbates, sorbitan esters, polyoxyl stearates and a mixture of two or more thereof.

9. The cationic ophthalmic emulsion according to claim 1, wherein said colloid particles have an average particle size of equal or less than 1 µm.

10. The cationic ophthalmic emulsion according to claim 1, comprising another pharmaceutically active substance, either in the oily core or in the aqueous part of the emulsion.

11. The cationic ophthalmic emulsion according to claim 10, wherein the another pharmaceutically active substance is selected from the group consisting of beta-blockers; inhibitors of carbonic anhydrase; sympathomimetics; parasympathomimetics; cholinesterase inhibitors; echothiophate and/or their derivatives; and/or optically acceptable salts thereof.

12. The cationic ophthalmic emulsion according to claim 1, which meets zeta potential stability Test B requirements, wherein the requirements comprise:

the difference between the zeta potential measured when the emulsion is prepared and the zeta potential measured after 48 hours of storage is less than the standard of error of measurement, wherein, the storage for 48 hours is in glass vials (Type I) of 10 ml effective capacity containing between 5-10 ml of the emulsion sealed under nitrogen atmosphere (without bubbling) at 80° C., and, the zeta potential is measured by electrophoretic mobility in an apparatus equipped with suitable software and calibrated with the supplied standard, where, the emulsion is diluted in double distilled water to obtain scattering intensity allowing optimal particle detection, a sample count rate between 100 to 1000 KCps is used in homodyne detection, three consecutive measurements are performed at 25° C. using a constant cell drive of 150 mV, the measurements are averaged, and the measurements are converted into zeta potential values through the Smoluchowsky equation, using the dielectric constants and viscosity of water.

13. The cationic ophthalmic emulsion according to claim 1, which meets zeta potential stability Test C requirements, wherein the requirements comprise:

the difference between the zeta potential measured when the emulsion is prepared and the zeta potential measured after 7 days of storage is less than the standard of error of measurement, wherein, the storage for 7 days is in glass vials (Type I) of 10 ml effective capacity containing between 5-10 ml of the emulsion sealed under nitrogen atmosphere (without bubbling) at 80° C., and, the zeta potential is measured by electrophoretic mobility in an apparatus equipped with suitable software and calibrated with the supplied standard, where, the emulsion is diluted in double distilled water to obtain scattering intensity allowing optimal particle detection, a sample count rate between 100 to 1000 KCps is used in homodyne detection, three consecutive measurements are performed at 25° C. using a constant cell drive of 150 mV, the measurements are averaged, and the measurements are converted into zeta potential values through the Smoluchowsky equation, using the dielectric constants and viscosity of water.

14. The cationic ophthalmic emulsion according to claim 1, which meets zeta potential stability Test D requirements, wherein the requirements comprise:

the difference between the zeta potential measured when the emulsion is prepared and the zeta potential measured after 14 days of storage is less than the standard of error of measurement, wherein, the storage for 14 days is in glass vials (Type I) of 10 ml effective capacity containing between 5-10 ml of the emulsion sealed under nitrogen atmosphere (without bubbling) at 80° C., and, the zeta potential is measured by electrophoretic mobility in an apparatus equipped with suitable software and calibrated with the supplied standard, where, the emulsion is diluted in double distilled water to obtain scattering intensity allowing optimal particle detection, a sample count rate between 100 to 1000 KCps is used in homodyne detection, three consecutive measurements are performed at 25° C. using a constant cell drive of 150 mV, the measurements are averaged, the measurements are converted into zeta potential values through the Smoluchowsky equation, using the dielectric constants and viscosity of water.

15. An ophthalmic formulation for treating ocular hypertension and/or for treating glaucoma comprising the cationic ophthalmic oil-in-water emulsion according to claim 1.

16. An ophthalmic formulation comprising the cationic ophthalmic oil-in-water emulsion according to claim 1, optionally in combination with an ophthalmologically acceptable carrier, said formulation being in the form of eye drops, eye ointment, or ophthalmic gel.

17. An ophthalmic formulation according to claim 15, comprising a pharmaceutically effective amount of an active ingredient in or within the ophthalmologically acceptable carrier.

18. A delivery device selected from the group consisting of lenses, an ocular patch, an implant, and an insert, said device containing an emulsion according to claim 1.

19. The cationic ophthalmic emulsion according to claim 3, wherein the concentration of the cetalkonium chloride is between 0.003 and 0.03%.

* * * * *